US012586180B2

(12) United States Patent     (10) Patent No.:   US 12,586,180 B2

Villard et al.     (45) Date of Patent:    Mar. 24, 2026

---

(54) ASSESSMENT OF IMAGE QUALITY FOR A MEDICAL DIAGNOSTICS DEVICE

(71) Applicant: AI Optics Inc., New York, NY (US)

(72) Inventors: Benjamin JJ Villard, Bethesda, MD (US); Luke Michael Moretti, New York, NY (US); Andrew DiGiore, New York, NY (US); Sayed Mazdak Abulnaga, Somerville, MA (US)

(73) Assignee: AI Optics Inc., New York, NY (US)

( * ) Notice: Subject to any disclaimer, the term of this patent is extended or adjusted under 35 U.S.C. 154(b) by 822 days.

(21) Appl. No.: 17/807,352

(22) Filed: Jun. 16, 2022

(65) Prior Publication Data

US 2022/0405927 A1    Dec. 22, 2022

Related U.S. Application Data

(60) Provisional application No. 63/202,642, filed on Jun. 18, 2021.

(51) Int. Cl.
   *G06N 20/00*     (2019.01)
   *A61B 3/00*      (2006.01)
        (Continued)

(52) U.S. Cl.
   CPC .......... *G06T 7/0012* (2013.01); *A61B 3/0008* (2013.01); *A61B 3/1208* (2013.01);
        (Continued)

(58) Field of Classification Search
   None
   See application file for complete search history.

(56) References Cited

U.S. PATENT DOCUMENTS

| | | | |
|---|---|---|---|
| 5,912,720 A | 6/1999 | Berger |
| 8,076,667 B2 | 12/2011 | Tansu |
| | (Continued) | | |

FOREIGN PATENT DOCUMENTS

| | | |
|---|---|---|
| IN | 201741018739 | 11/2018 |
| JP | 2020178903 | 11/2020 |
| | (Continued) | |

OTHER PUBLICATIONS

Center for Innovation (L V Prasad Eye Institute), Open Indirect Ophthalmoscope, https://lvpmitra.com/oio#introduction (2021).

(Continued)

*Primary Examiner* — Xuyang Xia

(74) *Attorney, Agent, or Firm* — Knobbe, Martens, Olson & Bear, LLP

(57) ABSTRACT

A medical diagnostic system can assess quality of a representation of a body part determined based on a response of the body part to exposure to electromagnetic waves, process the representation with a disease detection machine learning model to determine a certainty measure for a presence of a disease, determine a quality score for the representation based on the quality of the representation and the certainty measure, and discard the at least one representation based on the quality score. Combining machine learning in conjunction with one another, such as, for quality assessment and disease detection, can provide for more accurate image quality analysis, lead to faster medical imaging, and reduce the need to retake images or entirely re-perform medical imaging. The system can be easier to use, be more robust and faster than other systems by reducing the need to retake images while maintaining performance of the system.

20 Claims, 4 Drawing Sheets

(51) Int. Cl.

| | |
|---|---|
| *A61B 3/12* | (2006.01) |
| *A61B 3/14* | (2006.01) |
| *G06T 7/00* | (2017.01) |

(52) U.S. Cl.
CPC .............. *A61B 3/14* (2013.01); *G06N 20/00* (2019.01); *G06T 2207/10016* (2013.01); *G06T 2207/20081* (2013.01); *G06T 2207/30041* (2013.01); *G06T 2207/30168* (2013.01)

(56) References Cited

U.S. PATENT DOCUMENTS

| | | | |
|---|---|---|---|
| 8,687,862 B2 | 4/2014 | Hsu | |
| 8,817,172 B2 | 8/2014 | Jolma | |
| 8,960,910 B2 | 2/2015 | Alasaarela | |
| 9,033,507 B2 | 5/2015 | Alasaarela | |
| 9,757,031 B2 | 9/2017 | Wang | |
| 10,376,142 B2 | 8/2019 | Dirghangi | |
| D884,044 S | 5/2020 | Keinanen | |
| 11,950,847 B1 | 4/2024 | Moretti | |
| 12,193,746 B1 | 1/2025 | Moretti | |
| 2005/0234300 A1 | 10/2005 | Farrell | |
| 2011/0299036 A1 | 12/2011 | Goldenholz | |
| 2012/0130252 A1 | 5/2012 | Pohjanen | |
| 2012/0257163 A1 | 10/2012 | Dyer | |
| 2017/0013191 A1* | 1/2017 | Saad | G06V 20/35 |
| 2017/0065230 A1* | 3/2017 | Sinha | A61B 5/02438 |
| 2017/0209029 A1* | 7/2017 | Gazdzinski | A61B 1/00156 |
| 2018/0055357 A1* | 3/2018 | Meyerson | A61B 5/7282 |
| 2018/0153399 A1 | 6/2018 | Fink | |
| 2018/0160903 A1* | 6/2018 | Su | A61B 3/158 |
| 2018/0247020 A1 | 8/2018 | Itu | |
| 2019/0110753 A1 | 4/2019 | Zhang | |
| 2019/0133435 A1 | 5/2019 | Browne | |
| 2019/0216308 A1 | 7/2019 | Senaras et al. | |
| 2019/0272631 A1 | 9/2019 | Shemonski | |
| 2020/0170564 A1 | 6/2020 | Jiang | |
| 2020/0196869 A1 | 6/2020 | Narayanan | |
| 2020/0405148 A1 | 12/2020 | Tran | |
| 2021/0035301 A1 | 2/2021 | Soares | |
| 2022/0215541 A1* | 7/2022 | Paul | A61B 6/504 |
| 2022/0398718 A1* | 12/2022 | Rao | G06T 7/0002 |
| 2022/0405927 A1 | 12/2022 | Villard | |

FOREIGN PATENT DOCUMENTS

| | | |
|---|---|---|
| KR | 20190091857 | 8/2019 |
| KR | 102032193 | 10/2019 |
| KR | 20190129247 | 11/2019 |
| WO | WO 2016/179370 | 11/2016 |
| WO | WO 2017/031099 | 2/2017 |
| WO | WO 2020/173516 | 9/2020 |

OTHER PUBLICATIONS

Bleicher, Ariel, Teenage Whiz Kid Invents an AI System to Gianose her Grandfather's Eye Disease, IEEE Spectrum (2017). https://spectrum.ieee.org/the-human-os/biomedical/diagnostics/teenage-whiz-kid-invents-an-ai-system-to-diagnose-her-grandfathers-eye-disease.

Masumoto, et al, Deep-learning classifier with an ultrawide-field scanning laser ophthalmoscope detects glaucoma visual field severity, Glaucoma Journal 27(7):647-652 (2018).
Ting, et al., Artificial intelligence and deep learning in ophthalmology, Br J. Ophthalmol 103:167-175 (2019).
WelchAllyn Standard Ophthalmoscope (https://www.welchallyn.com/en/products/categories/physical-exam/eye-exam/ophthalmoscopes--traditional-direct/35v_standard_ophthalmoscope.html#_) 2018.
WelchAllyn PanOptic Brochure (2016).
WelchAllyn iExaminer (https://www.welchallyn.com/en/microsites/iexaminer.html) 2018.
D-Eye Smartphone-Based Retinal Imaging System (https://www.d-eyecare.com/en_US/product#features) (retrieved in Mar. 2021).
Horus 100 fundus camera (http://www.miis.com.tw/product01.php?no=36) 2014.
Horus 200 portable fundus camera (http://www.miis.com.tw/product01.php?no=84) 2014.
Microclear Luna Fundus Camera (https://www.microcleartech.com/en/productInfo?p=hfc_v2) (retrieved in Mar. 2021).
Mediworks FC 161 hand-held fundus camera (https://www.mediworks.biz/en/product/handheld-fundus-camera-fc161).
Remidio NMFOP (https://www.remidio.com/fop.php) (retrieved in Mar. 2021).
Welch Allyn RetinaVue 700 Imager (2019).
IDx-DR Autonomous AI (https://dxs.ai/products/dermatology/autonomous-ai/) 2020.
IDx-DR Overview: Close Care Gaps, Prevent Blindness (https://dxs.ai/products/idx-dr/idx-dr-overview/) 2020.
EyeNuk EyeArt screening system (https://www.eyenuk.com/en/) (retrieved in Mar. 2021).
Chuan, G., Pleiss, G., Sun, Y., and Weinberger, K, Q. "On calibration of modern neural networks." In International Conference on Machine Learning, pp. 1321-1330. PMLR, 2017.
Gal, Y. Uncertainty in deep learning.: University of Cambridge, 1(3), 4 (2016).
Kendall, A, and Gal, Y. "What Uncertainties Do We Need in Bayesian Deep Learning for Computer Vision?" In Advances in Neural Information Processing Systems, 30, 2017.
"Bringing eye screenings to the masses" (2020) (https://cordis.europa.eu/article/id/422126-bringing-eye-screenings-to-the-masses).
"The new era of eyecare" (2017) (https://news.cision.com/optomed/r/the-new-era-of-eye-care,c2361383).
Abramoff et al., Pivotal trial of an autonomous AI-based diagnostic system for detection of diabetic retinopathy in primary care offices, 39 npj Digital Medicine 1 (2018).
Optomed Aurora IQ Handheld Fundus Camera brochure.
Optomed Aurora User Manual (2020).
Optomed Prospectus https://www.optomed.com/wp-content/uploads/2019/11/Optomed-Plc-Prospectus-21-November-2019.pdf, Nov. 21, 2019.
Rajalakshmi et al., Automated diabetic retinopathy detection in smartphone-based fundus photography using artificial intelligence, Eye 32:1138-1144 (2018) DOI: 10.1038/s41433-018-0064-9.
Reeta, Fundus imaging and the use of artificial intelligence in the screening of diabetic retinopathy. R Oulu University of Applied Sciences (Fall 2018).
Savoy, Idx-DR for Diabetic Retinopathy Screening, American Family Physician 101(5):307-308 (2020).
Schmidt-Erfurth et al., Artificial intelligence in retina, 67 Progress in Retinal and Eye Research 1-29 (2018).

* cited by examiner

ASSESSMENT OF IMAGE QUALITY FOR A MEDICAL DIAGNOSTICS DEVICE

CROSS-REFERENCE TO RELATED APPLICATIONS

This application claims priority to U.S. Provisional Patent Application No. 63/202,642, filed on Jun. 18, 2021, which is incorporated by reference is its entirety.

TECHNICAL FIELD

Disclosed are medical diagnostics devices, such as retina cameras, that perform assessment of image quality, diagnose a disease, or aid in clinical decision making, for example, using artificial intelligence (AI).

BACKGROUND

Medical diagnostics devices are becoming ubiquitous. For instance, a fundus (or retina) camera is an instrument for inspecting the retina of the eye. Many ophthalmologic, neurologic, and systemic diseases can cause structural abnormalities in the retina, which alter the visual appearance of the retina. These structural and visible abnormalities are known as biomarkers, and they may indicate the presence or absence of a disease. For example, diabetics have high levels of circulating blood sugar that, over time, can cause damage to the small vessels in the retina and lead to the formation of microaneurysms. Such microaneurysms indicate the presence of diabetic retinopathy. Clinicians use fundus cameras to visualize and assess a patient's retina for biomarkers in order to diagnose the disease. Assessment of image quality is important for ensuring accuracy of a medical diagnostics device. As a result, improvements in the assessment of image quality can be beneficial.

BRIEF DESCRIPTION OF DRAWINGS

Various aspects of the disclosure will now be described with regard to certain examples and implementations, which are intended to illustrate but not limit the disclosure.

Throughout the drawings, reference numbers may be re-used to indicate correspondence between referenced elements. The drawings are provided to illustrate example implementations described herein and are not intended to limit the scope of the disclosure.

SUMMARY

Figure 1:
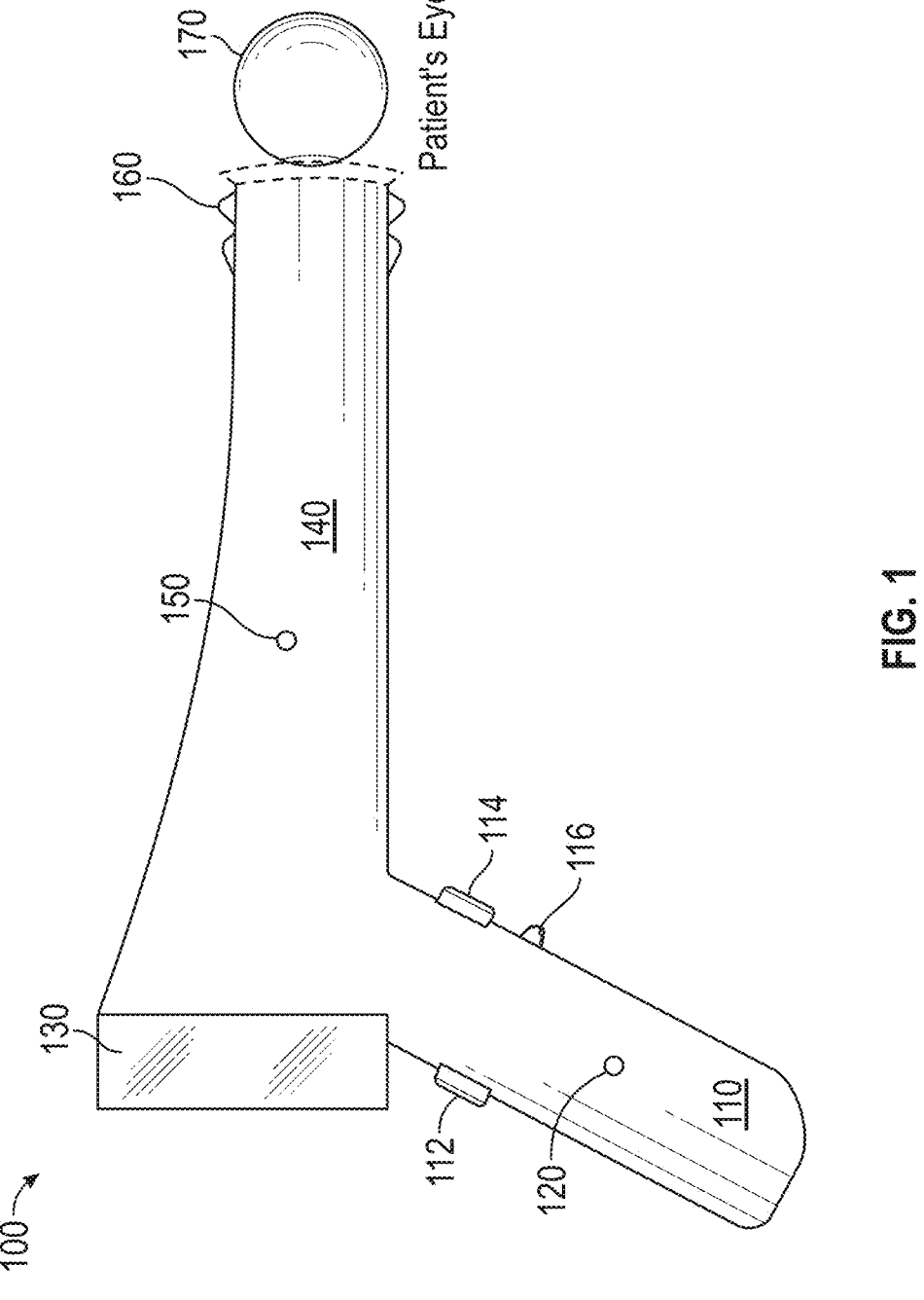
FIG. 1 illustrates a retina camera.

A retina camera can include a housing with a body and a handle. The handle can be connected to the body and configured to be held by a user. The retina camera can include a light source supported by the housing. The light source can be configured to irradiate an eye of a patient with light. The retina camera can include imaging optics supported by the housing. The imaging optics can be configured to receive light reflected by the eye. The retina camera can include an image detector array configured to receive light from the imaging optics and to sense the received light. The retina camera can include electronic processing circuitry supported by the housing. The electronic processing circuitry can be configured to generate at least one image of the eye based on signals received from the image detector array. The electronic processing circuitry can be configured to assess an image quality of the at least one image; process the at least one image with a dedicated machine learning model to determine a certainty measure for a presence of at least one disease from a plurality of diseases that the dedicated machine learning model has been trained to identify. The electronic processing circuitry can be configured to determine a quality score for the at least one image based on the image quality of the at least one image and the certainty measure. The electronic processing circuitry can be configured to, responsive to a determination that the quality score does not satisfy a quality threshold, discard the at least one image.

The retina camera of any of the preceding paragraphs and/or any of the retina cameras disclosed herein can include one or more of the following features. The dedicated machine learning model can determine the presence of the at least one disease. A separate machine learning model which can assess the quality of an image. Each of the machine learning models can be a single model or a number of machine learning models, which can be combined to assess either the presence of the at least one disease or the quality of an image. The electronic processing circuitry can be configured to, responsive to a determination that the quality score satisfies an image quality threshold (which can be static or dynamic), provide an indication of the presence of the at least one disease. The retina camera can have a display at least partially supported by the housing. The electronic processing circuitry can be configured to provide the indication of the presence of the at least one disease on the display. Discarding the at least one image can cause the at least one image to be retaken. The image quality can be assessed based on a probability that the image quality is sufficient. The image quality can be assessed based on a confidence score that the image quality is sufficient. The certainty measure can be based on a probability generated by the dedicated machine learning model. The certainty measure can be determined based on a confidence score generated by the dedicated machine learning model. The at least one image can include a plurality of images determined from a video of the eye, and wherein discarding the at least one image can cause use of another image from the plurality of images for detecting the presence of the at least one disease.

The retina camera of any of the preceding paragraphs and/or any of the retina cameras disclosed herein can include one or more of the following features. The electronic processing circuitry can be configured to assess the image quality of the at least one image with a secondary machine learning model different from the image quality dedicated machine learning model. This secondary machine learning model is dedicated to assess the presence or absence of the at least one image. Each task dedicated machine learning model can be a combination of machine learning models. The electronic processing circuitry can be configured to determine the quality score for the at least one image based on the image quality of the at least one image and the certainty measure by, responsive to the certainty measure for the presence of the at least one disease satisfying a threshold, setting the quality score to satisfy the quality threshold irrespective of the image quality. The electronic processing circuitry can be configured to determine the quality score for the at least one image based on the image quality of the at least one image and the certainty measure by, responsive to the certainty measure not satisfying a threshold, setting the quality score to not satisfy the quality threshold irrespective of the image quality. The electronic processing circuitry can be configured to determine the quality score for the at least one image based on the image quality of the at least one image and the certainty measure by, responsive to the image quality not satisfying an image quality threshold, setting the quality score to not satisfy the quality threshold irrespective of the certainty measure. The electronic processing circuitry can be configured to determine the quality score for the at least one image based on the image quality of the at least one image and the certainty measure by, responsive to the image quality satisfying an image quality threshold, setting the quality score to satisfy the quality threshold irrespective of the certainty measure. The electronic processing circuitry can include at least one processor.

The dedicated machine learning models can work together in a symbiotic relationship instead of a serial manner to assess the quality of the at least one image through a dedicated process called a decision maker. While the image quality dedicated machine learning model may classify if an image is of good or bad quality, it can also incorrectly classify images of good quality, or images where the image quality dedicated model is able to make predictions confidently. When using a secondary disease detection dedicated machine learning model, the overall performance of the machine learning models can be dependent on the symbiotic relationship of the machine learning models, and as such, any optimization of this symbiotic relationship may be made by taking into account the performance of both models as a whole (through the machine learning parameters or hyperparameters, for example). As machine learning (ML)/deep learning (DL) disease detection algorithms can also have a high degree of false confidence in their prediction, which can lead to a large number of false positives and false negatives, by assessing the combination of all ML/DL models as whole, a better outcome can be obtained. For example, the disease detection machine learning model may assign the presence of disease in an unrelated image (for example, of an eyelid), while the image quality machine learning model may assign a high confidence that the image is of low quality and/or a low probability that the image is of sufficient quality. In these cases, the image quality machine learning method can override the disease detection algorithm, and the image can be retaken. In another example, the disease detection machine learning model can assign a high probability and a high confidence that the at least one image contains the presence or absence, of a disease, while the image quality machine learning model outputs a moderate probability, which falls under the classification threshold, indicating that the at least one image would not pass the image quality check. In this scenario the image would not have to be retaken, as the disease detection machine learning model would be correct in its prediction. Advantageously, the using the dedicated machine learning models in conjunction with one another, such as by using the decision maker, can provide for more accurate image quality analysis, lead to faster medical imaging procedures, and reduce the need to retake images or entirely re-perform medical imaging procedures. Real-time imaging diagnostics devices or systems can be easier to use, be more robust and faster than other systems by reducing the need to retake images while maintaining performance of the diagnostic system.

The present disclosure provides a method of operating the retina camera of any of the preceding paragraphs and/or any of the retina cameras disclosed herein.

The present disclosure provides a non-transitory computer readable medium storing instructions that, when executed by at least one processor, cause the at least one processor to implement a method of operating a retina camera of any of the preceding paragraphs and/or any of the retina cameras disclosed herein.

A medical diagnostics system can include an energy source configured to direct electromagnetic waves toward a body part of a patient. The medical diagnostics system can include a detector configured to sense a response of the body part to the electromagnetic waves. The medical diagnostics system can include electronic processing circuitry configured to generate at least one representation of the body part based on the response sensed by the detector. The electronic processing circuitry can be configured to assess a quality of the at least one representation. The electronic processing circuitry can be configured to process the at least one representation with a disease detection dedicated machine learning model to determine a certainty measure for a presence of at least one disease from a plurality of diseases that the disease detection dedicated machine learning model has been trained to identify. The electronic processing circuitry can be configured to determine a quality score for the at least one representation based on the quality of the at least one representation and the certainty measure. The electronic processing circuitry can be configured to discard the at least one representation based on the quality score not satisfying a representation quality threshold.

The medical diagnostics system of any of the preceding paragraphs and/or any of the medical diagnostics systems disclosed herein can include one or more of the following features. The at least one representation can include an image of the body part. The energy source can include a light source, an x-ray source, or a magnetic source. The energy source can include a light source, the detector can include an image detector array, the body part can include an eye, and the at least one representation can include at least one image of the eye. The disease detection dedicated machine learning model can determine the presence of the at least one disease. The electronic processing circuitry can be configured to, responsive to a determination that the quality score satisfies an image quality threshold, provide an indication of the presence of the at least one disease. The medical diagnostics system can include a display, wherein the electronic processing circuitry can be configured to provide the indication of the presence of the at least one disease on the display. The at least one image can include a plurality of images determined from a video of the eye, and wherein discarding the at least one representation can cause using of another image from the plurality of images for detecting the presence of the at least one disease.

The medical diagnostics system of any of the preceding paragraphs and/or any of the medical diagnostics systems disclosed herein can include one or more of the following features. Discarding the at least one representation can cause the at least one representation to be retaken. The electronic processing circuitry can be configured to assess the quality of the at least one representation with a machine learning model dedicated to the image quality task, and which is different from the machine learning model dedicated to disease detection. The disease detection dedicated machine learning model can determine the presence of the at least one disease. The electronic processing circuitry can be configured to, responsive to a determination that the quality score satisfies a quality threshold, provide an indication of the presence of the at least one disease. The electronic processing circuitry can be configured to determine the quality score for the at least one representation based on the quality of the at least one representation and the certainty measure by, responsive to the certainty measure for the presence of the at least one disease satisfying a confidence threshold, not discarding the at least one representation irrespective of the quality of the at least one representation satisfying the representation quality threshold. The electronic processing circuitry can be configured to determine the quality score for the at least one representation based on the quality of the at least one representation and the certainty measure for the presence of the at least one disease by, responsive to the quality of the at least one representation not satisfying the representation quality threshold, discarding the at least one representation irrespective of the certainty measure for the presence of the at least one disease satisfying a disease presence threshold. The electronic processing circuitry can include at least one processor. The image quality dedicated machine learning model and the disease detection dedicated machine learning model can work together in a non sequential manner to assess the quality of an image through the decision making process.

The present disclosure provides a method of operating a medical diagnostics system of any of the preceding paragraphs and/or any of the medical diagnostics systems disclosed herein.

The present disclosure provides a non-transitory computer readable medium storing instructions that, when executed by at least one processor, cause the at least one processor to implement a method of operating a medical diagnostics system of any of the preceding paragraphs and/or any of the medical diagnostics systems disclosed herein.

DETAILED DESCRIPTION

Introduction

A device (or instrument) with integrated artificial intelligence (AI) can be used to assess a patient's body part to detect a disease. The device can be portable, such as handheld. For example, the device can be a retina camera configured to assess a patient's eye (or retina) and, by using an on-board AI retinal disease detection system, provide real-time analysis and diagnosis of disease that caused changes to the patient's retina. Easy and comfortable visualization of the patient's retina can be facilitated using such retina camera, which can be placed over the patient's eye, display the retina image on a high-resolution display, analyze at least one captured image by the on-board AI system, and provide determination of presence of a disease.

As another example, the device can be an otoscope configured to assess a patient's ear and, by using an on-board artificial intelligence (AI) ear disease detection system, possibly provide immediate analysis and/or diagnosis of diseases of the patient's ear. Such an otoscope can have one or more advantages described above or elsewhere in this disclosure. As yet another example, the device can be a dermatology scope configured to assess a patient's skin and, by using an on-board artificial intelligence (AI) skin disease detection system, possibly provide immediate analysis and/or diagnosis of diseases of the patient's skin. Such a dermatology scope can have one or more advantages described above or elsewhere in this disclosure.

Artificial intelligence (AI) (for example, machine-learning (ML) and deep-learning (DL)) can be used to create algorithms or machine learning models (sometimes referred to as models) to analyze medical images for disease screening, diagnosis, prognostication and monitoring. A subset of such AI models can also be referred to as classifiers. Common machine learning tasks fall under various categories, such as regression, classification, clustering, transcription, or anomaly detection, among several others. This disclosure interchangeably refers to a classifier as a general term inclusive of all machine learning models as well as the subset of machine learning models. Classifiers can use an image as an input and classify the image into a certain category or class based on what the model has been designed to detect. Some classification models can be detection models designed to detect whether a condition exists or not, for example whether a patient has a disease or not. The classification result can be an output of the classifier. Alternatively, classifiers can classify regions of interest within an image. One example of a classification result could be the presence or absence of disease or biomarkers. In some cases, in order for these classifiers to perform optimally (such as, with the highest sensitivity/specificity) and produce a useful output, it may be important to assess the quality of the medical image that is being used as an input.

When an image is run through a classifier, the classifier can provide an output, regardless of the quality or relevance of the input. Therefore, for certain medical image analysis tasks it may be important to first assess the quality or relevance of the image that is going to be classified. This leads to a higher likelihood that the classifier evaluates relevant and/or sufficient quality images, which, in turn, increases the likelihood that the classifier outputs an accurate classification. If image quality is not first evaluated, the classifier performance can be negatively impacted. The classifier output can be less reliable, impacting the decisions and/or outcomes based on the output. In this context, the classifier may make a prediction that it deems to be correct, despite the fact that the image may have artifacts or contain other characteristics of a poor quality image that could affect classification analysis. The classifier may make a prediction and output a high confidence score to indicate that it deems the classification result to be correct. In the case of disease detection for example, the classifier may output a probability of containing the disease.

For example, when a patient with diabetes is having their retina evaluated for the presence of diabetic retinopathy (DR), a photo of their retina can be captured and the retinal image will be run through a classifier designed to evaluate retinal photos to detect the presence of DR. A machine learning model designed to detect a disease can also be referred to as a disease detection (DD) model. In this scenario, it may be important that the image is first assessed for quality or relevance before being input into a DR model (or a DR DD model). For example, a patient could blink during the image capture process such that the camera captured a photo of the patient's eyelid instead of the retina. That eyelid photo could be input into the DR classifier and the classifier would still provide a classification result, leading to a misrepresentative diagnosis. Instead, with the use of prior image quality assessment, the eyelid photo would be designated as an image that is not a photo of the retina and, thus, irrelevant. The lack of prior image quality assessment (IQA) in this scenario would negatively affect the performance of the downstream classifier and the utility of the classification output because the patient's retina was not truly assessed for disease because the image was of the eyelid. Thus, an accurate determination of whether the patient's retina has DR cannot be made. This example highlights how the relevance of an input can negatively affect the performance and utility of a classifier.

Additionally, the image quality also affects the performance and utility of the classifier. For example, if this patient's retinal image was captured, but it was of very bad quality (e.g., blurry, out of focus, low resolution, significant shadowing, artifacts, poor retinal visibility, etc.), then the disease detection result may be negatively affected. The DD model could mistake some or all of the artifacts from the low quality image as an indication of a disease or biomarker.

In the above examples, IQA prior to disease detection would have resulted in a determination that the image was of inadequate or insufficient quality for interpretation. This can indicate that a new image of the patient's retina needs to be captured (or another previously captured image should be used) before a reliable DR assessment can be made. Machine learning models can oftentimes make predictions with a high degree of confidence, despite the fact that 1) the image may be of poor quality, 2) the image may be from an entirely different source (for example, a different body part, anatomy, structure, object, or device), and 3) the image may have been of the same source but never seen during training. An image that may have been of the same source, but never seen during training, can be considered out of distribution. Distribution can refer to the variability of the input that a model is trained on, such that "out of distribution" can refer to input is that something is outside the range of inputs that the model was trained on. For example, if a classification model is trained to detect skin conditions, but it was only trained using images of people with lighter skin tones, new input images of people with darker skin tones would be out of distribution because the model was not trained on such inputs.

Implementations of the image quality assessment system described herein can benefit the field of medical image analysis by serving as an optimal system that allows for minimal retaking of images, while obtaining the best diagnostic performance. The image quality assessment system described herein can be applied to any image analysis.

AI models, such as DD models and IQA models, can output a probability and/or a confidence score. An AI model can output that there is a high probability and a high confidence in its output predictions, or the AI model can output a high probability and a low confidence in its output predictions. In some implementations, the probabilistic outputs can be used as a proxy measurement of the confidence of the network in that probability. However, in most cases, the inherent meanings differ and are uncalibrated with the true label predictions.

Disclosed are implementations of systems and methods for combining the machine learning model's outputs and/or confidence scores of a DD model and IQA model to ensure optimal system performance and reduce the need to repeat and/or prolong a medical imaging procedure. In some cases, the output can be probabilistic. In some cases, a system can make a holistic decision whether to i) trust the acquired image as sufficient quality and/or ii) trust the predicted disease detection output.

Retina Camera with On-Board AI

FIG. 1 illustrates an example retina camera 100. A housing of the retina camera 100 can include a handle 110 and a body 140 (in some cases, the body can be barrel-shaped). The handle 110 can optionally support one or more of power source, imaging optics, or electronics 120. The handle 110 can also possibly support one or more user inputs, such as a toggle control 112, a camera control 114, an optics control 116, or the like. Toggle control 112 may be used to facilitate operating a display 130 in case of a malfunction. For example, toggle control 112 can facilitate manual scrolling of the display, switching between portrait or landscape mode, or the like. Toggle control 112 can be a button. Toggle control 112 can be positioned to be accessible by a user's thumb. Camera control 114 can facilitate capturing at least one image (or video). Camera control 114 can be a button. Camera control 114 can be positioned to be accessible by a user's index finger (such as, to simulate action of pulling a trigger) or middle finger. Optics control 116 can facilitate adjusting one or more properties of imaging optics, such as illumination adjustment, aperture adjustment, focus adjustment, zoom, etc. Optics control 116 can be a button or a scroll wheel. For example, optics control 116 can focus the imaging optics. Optics control 116 can be positioned to be accessible by a user's middle finger or index finger.

The retina camera 100 can include the display 130, which can be a liquid crystal display (LCD) or other type of display. The display 130 can be supported by the housing as illustrated in FIG. 1. For example, the display 130 can be positioned at a proximal end of the body 140. The display 130 can be one or more of a color display, high resolution display, or touch screen display. The display 130 can reproduce one or more images (or video) of the patient's eye 170. The display 130 can allow the user to control one or more image parameters, such as zoom, focus, or the like. The body 140 can support one or more of the power source, imaging optics, imaging sensor, imaging detector, electronics 150 or any combination thereof.

A cup 160 can be positioned on (such as, removably attached to) a distal end of the body 140. The cup 160 can be made at least partially from soft and/or elastic material for contacting patient's eye orbit to facilitate examination of patient's eye 170. For example, the cup can be made of plastic, rubber, rubber-like, or foam material. Accordingly, the cup 160 may be compressible. The cup 160 can also be disposable or reusable. In some cases, the cup 160 can be sterile. The cup 160 can facilitate one or more of patient comfort, proper device placement, blocking ambient light, or the like. Some designs of the cup may also assist in establishing proper viewing distance for examination of the eye and/or pivoting for panning around the retina.

Figure 2:
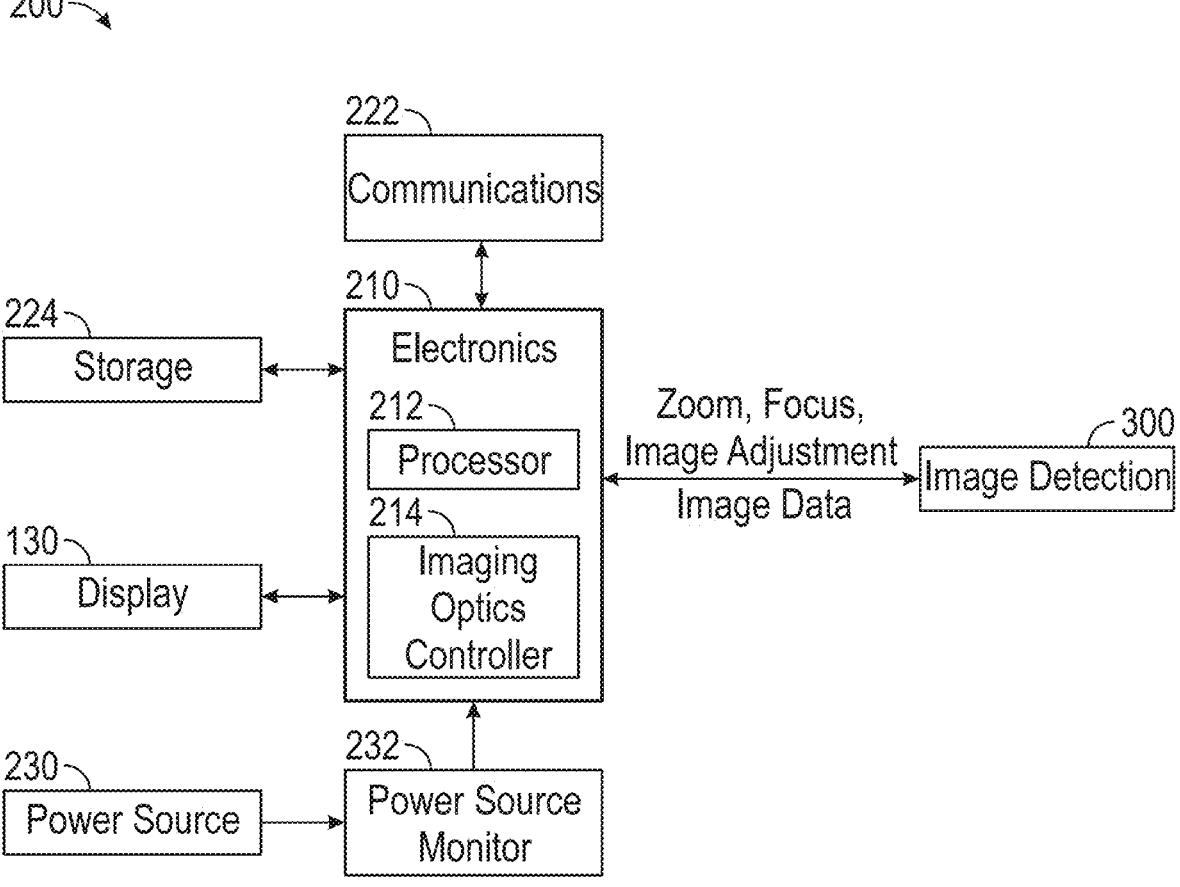
FIG. 2 schematically illustrates a system level diagram showing retina camera components of FIG. 1.

FIG. 2 illustrates a block diagram 200 of various components of the retina camera 100. Power source 230 can be configured to supply power to electronic components of the retina camera 100. Power source 230 can be supported by the handle 110, such as positioned within or attached to the handle 110 or be placed in another position on the retina camera 100. Power source 230 can include one or more batteries (which may be rechargeable). Power source 230 can receive power from a power supply (such as, a USB power supply, AC to DC power converter, or the like). Power source monitor 232 can monitor level of power (such as, one or more of voltage or current) supplied by the power source 230. Power source monitor 232 can be configured to provide one or more indications relating to the state of the power source 230, such as full capacity, low capacity, critical capacity, or the like. One or more indications (or any indications disclosed herein) can be visual, audible, tactile, or the like. Power source monitor 232 can provide one or more indications to electronics 210.

Electronics 210 can be configured to control operation of the retina camera 100. Electronics 210 can include one or more hardware circuit components (such as, one or more controllers or processors 212), which can be positioned on one or more substrates (such as, on a printed circuit board). Electronics 210 can include one or more of at least one graphics processing unit (GPU) or at least one central processing unit (CPU). Electronics 210 can be configured to operate the display 130. Storage 224 can include memory for storing data, such as image data (which can include one or more images or video) obtained from the patient's eye 170, one or more parameters of AI detection, or the like. Any suitable type of memory can be used, including volatile or non-volatile memory, such as RAM, ROM, magnetic memory, solid-state memory, magnetoresistive random-access memory (MRAM), or the like. Electronics 210 can be configured to store and retrieve data from the storage 224.

Communications system 222 (sometimes referred to as an interface) can be configured to facilitate exchange of data with another computing device (which can be local or remote). Communications system 222 can include one or more of antenna, receiver, or transmitter. In some cases, communications system 222 can support one or more wireless communications protocols, such as WiFi, Bluetooth, NFC, cellular, or the like. In some instances, the communications system can support one or more wired communications protocols, such as USB. Electronics 210 can be configured to operate communications system 222. Electronics 210 can support one or more communications protocols (such as, USB) for exchanging data with another computing device.

Electronics 210 can control an image detection system 300, which can be configured to facilitate capturing of (or capture) image data of the patient's eye 170. Electronics 210 can control one or more parameters of the image detection system 300 (for example, zoom, focus, aperture selection, image capture, provide image processing, or the like). Such control can adjust one or more properties of the image of the patient's eye 170. Electronics 210 can include an imaging optics controller 214 configured to control one or parameters of the image detection system 300. Imaging optics controller 214 can control, for example, one or more motor drivers of the image detection system 300 to drive motors (for example, to select an aperture, to select lenses that providing zoom, to move of one or more lenses to provide autofocus, to move a detector array 380 or image sensor or detector to provide manual focus or autofocus, or the like). Control of one or more parameters of the image detection system 300 can be provided by one or more of user inputs (such as a toggle control 112, a camera control 114, an optics control 116, or the like), display 130, etc. Image detection system 300 can provide image data (which can include one or more images or video) to electronics 210. As disclosed herein, electronics 210 can be supported by the retina camera 100. The electronics 210 may not be configured to be attached to (such as, connected to) another computing device (such as, mobile phone or server) to perform determination of presence of a disease.

Image Quality Assessment

When an image is run through a machine learning model, such as a classifier (which, as described herein, can implement one or more machine learning models), the model can provide an output regardless of the quality or relevance of the input. Therefore, for certain medical image analysis tasks it may be important to first assess the quality or relevance of the image that is going to be classified. This can be referred to as image quality assessment (IQA). This leads to a higher likelihood that the image quality machine learning model evaluates relevant and/or sufficient quality images, which, in turn, increases the likelihood that the disease detection machine learning model outputs an accurate classification. If image quality is not first evaluated, the disease detection machine learning model performance can be negatively impacted. The machine learning model output can be less reliable, impacting the decisions and/or outcomes based on the output. In this context, the machine learning model, such as a classifier, may make a prediction that it deems to be correct, despite the fact that the image may have artifacts or contain other characteristics of a poor quality image that could affect classification analysis. The machine learning model may make a prediction and output a high confidence score to indicate that it deems the machine learning model's result, such as the disease detection machine learning model, to be correct despite the fact that 1) the image may be of poor quality, 2) the image may be from an entirely different source (for example, a different body part, anatomy, structure, object, or device), and 3) the image may have been of the same source but never seen during training. An image that may have been of the same source but never seen during training can be considered out of distribution.

Classifiers have two main types of uncertainty: epistemic uncertainty and aleatoric uncertainty. Epistemic uncertainty, sometimes called systematic uncertainty, refers to the uncertainty introduced by the assumptions of the model. Epistemic uncertainty may occur due to the model not training on a sufficiently large amount of data. Aleatoric uncertainty, sometimes called statistical uncertainty, occurs when there is noise in the inputs to the model. Aleatoric uncertainty may occur from a poor measurement process for the inputs to the model. Having a proper IQA method can aid with the epistemic uncertainty, as it can properly filter the data that a model sees, ensuring that the model is well trained to the data it is likely to encounter.

In some implementations, IQA models can output a probability and/or a confidence score. An IQA model can output that there is a high probability and a high confidence in its output predictions, or the IQA model can output a high probability and a low confidence in its output predictions. In some implementations, the probabilistic outputs can be used as a proxy measurement of the confidence of the network in that probability. However, in most cases, the inherent meanings differ and are uncalibrated with the true label predictions. An example true label prediction could be the manual labeling of images by an expert, or adjudication by a group of experts. For example, in the case of pneumonia classification from a chest X-ray, the network may make a prediction of the presence of pneumonia with a high probability and/or a high degree of confidence, even in the case where the image is too degraded or has too many artifacts that would make it ungradable by a physician. The physician may feel they need another image to properly diagnose and classify whether pneumonia is present. When the model has such high confidence in its output predictions, the model could either 1) have never seen an image of this quality before, 2) not have enough information to make a proper prediction, or 3) could be correct in its prediction. In other cases, the neural network model may make a prediction with low or medium confidence, for example with a probability of presence of pneumonia just above the cutoff threshold. The low confidence may be due to poor image quality, but the network still provides an output of the X-ray containing pneumonia. In this case, pre-filtering the image may have prevented a possible false positive.

An IQA model can be used to assess the quality of images. For example, if any of the images is determined to be of poor quality (for instance, as compared to a quality threshold), the user can be notified, the user may be guided to retake the image, the image may be tagged as poor quality, the image may not be stored, or the like. Image quality can be determined based on one or more of brightness, sharpness, contrast, color accuracy, distortion, noise, dynamic range, tone reproduction, or the like.

IQA methods for evaluating image quality can be separated into three primary categories: human, automatic, or semi-automatic evaluation. All three categories have the objective of evaluating an image and deciding if the image is of sufficient quality for subsequent interpretation/classification. If the image is not of sufficient quality, another image may be needed.

Human evaluation may require manual assessment by a person, usually an expert. An individual makes a decision with regards to the quality of the image. The outcome of this method also often serves as the ground truth labels on which the automatic and semi-automatic methods are built.

Automatic evaluation may be performed solely by an algorithm run on a computing device. IQA determination can be autonomous and thus may not require human input. Autonomous methods for IQA can include using combinations of one or more pre-defined thresholds for one or more imaging modality specific features, such as brightness limits, sharpness evaluation, field-of-view, extent of anatomy contained within an image, etc. Autonomous methods for IQA can also use various ML/DL methods for IQA. An example can include using convolutional neural network (CNN)-based classifiers that learn image features to classify the image quality based on labels. Another example can include ML models such as support vector machines that classify based on derived image features such as blur and sharpness, illumination, and the presence of anatomy. IQA models can be trained in a supervised manner where humans provide ground truth labels. IQA models can also be trained in an unsupervised manner. In the unsupervised method, an IQA model can be trained by letting the network learn what consists of a "good" image quality. Some systems can employ a combination of autonomous IQA methodologies, e.g., employing various combinations of simple feature thresholds with more complex ML/DL methods with the same end goal of determining if an image is of sufficient quality for subsequent classification. Autonomous IQA assessment combined with autonomous image classification allows for a completely autonomous pipeline for image analysis following image acquisition. Minimizing human involvement can increase efficiencies and improve the efficacy of image analysis by reducing inter- or intra-user variability.

Semi-automatic evaluation can include evaluation by an algorithm run on a computing device with some approval, check, or input from a human. Examples of semi-automatic evaluation include 1) the IQA algorithm may require the human to select a region of interest in the image, such as the optical disk in retinal fundus images, before outputting the IQA result, or 2) the model might require a final check from the user. The final check could be used to further enhance the performance of the IQA model in a continuous manner. In some implementations, a final check from the user may be only required based on the output of the IQA; for example, if the IQA classifies an image as sufficient quality it may require the user to confirm this classification, but not require the user to confirm an insufficient quality classification result.

IQA methods can provide insight into if an image is acceptable for further analysis, however they may not be optimized for use with a ML and/or DL classifiers. For example, ML/DL disease detection classifiers may still be able to detect disease in an image that would be classified as poor quality by IQA methods. Thus, an IQA model may unnecessarily identify images as poor quality that may otherwise have been successfully analyzed by the disease detection classification algorithm. In this situation, users may be forced to unnecessarily repeat and/or prolong a medical imaging procedure when the prior image or images were sufficient for disease detection. While the image quality assessment module may assist by pre-filtering images, it can incorrectly remove images of good quality, or images where the classifier is able to make predictions confidently. Furthermore, if the desired output of the system is for DL disease detection, the overall performance of the system can be dependent on the symbiotic relationship of the two models, and as such, any optimization of the algorithms parameters or hyperparameters may be made by taking into account the performance of both models as a whole.

Different IQA models can be trained on different types of images and use different types of images as inputs. For example, an IQA model may be trained on MRI images and use MRI images as inputs while another IQA model may be trained on CT images and use CT images as inputs. Although the forgoing provides one or more examples of images including retinal images, IQA models are not so limited, but can be extended to any image, especially images used for medical diagnostics, such as X-Ray images, computed tomography (CT) images, non-contrast head CT images (NCHCT), images taken using magnetic resonance imaging (MM), or the like.

With reference to FIG. 2, electronics (or electronic processing circuitry) 210 can include one or more controllers or processors configured to use one or more IQA models to analyze one or more images to determine if the image is of sufficient quality or not.

Disease Detection

Additionally or alternatively, electronics 210 can include one or more controllers or processors configured to analyze one or more images to identify a disease. For example, electronics 210 can include a processing system (such as, a Jetson Nano processing system manufactured by NVIDIA or a Coral processing system manufactured by Google), a System-on-Chip (SoC), or a Field-Programmable Gate Array (FPGA) to analyze one or more images. One or more images (or photographs) can be captured, for example, by the user operating the camera control 114 and stored in the storage 224.

One or more machine learning models can be used to analyze one or more images. One or more machine learning models can be trained using training data that includes images of subjects having various diseases of interest, such as retina disease (retinopathy, macular degeneration, macular hole, retinal tear, retinal detachment, or the like), ocular disease (cataracts or the like), systemic disease (diabetes, hypertension, or the like), Alzheimer's disease, etc. For example, any of the machine learning models can include a convolutional neural network (CNN), decision tree, support vector machine (SVM), regressions, random forest, or the like. One or more machine learning models can be trained to determine the presence of one or more diseases. Training of one or more models can be performed using many annotated images (such as, hundreds of images, thousands of images, tens of thousands of images, hundreds of thousands of images, or the like).

One or more machine learning models can determine the presence of a disease based on the output of one or more models. As described herein, images can be analyzed by one or more machine learning models one at a time or in groups to determine presence of the disease. When images are analyzed one at a time, determination of presence of the disease can be made in response to output of one or more models. When images are analyzed in a group, determination of presence of the disease can be made in response to combined outputs of one or more models analyzing the group of images.

In some implementations, DD models can output a probability and/or a confidence score. A DD model can output that there is a high probability and a high confidence in its output predictions, or the DD model can output a high probability and a low confidence in its output predictions. In some implementations, the probabilistic outputs can be used as a proxy measurement of the confidence of the network in that probability. However, in most cases, the inherent meanings differ and are uncalibrated with the true label predictions. In some implementations, probabilities and confidence scores can be considered a certainty measure.

Different DD models can be trained on different types of images and use different types of images as inputs. For example, an DD model may be trained on MM images and use MRI images as inputs while another DD model may be trained on CT images and use CT images as inputs. Although the forgoing provides one or more examples of images including retinal images, DD models are not so limited, but can be extended to any image, especially images used for medical diagnostics, such as X-Ray images, computed tomography (CT) images, non-contrast head CT images (NCHCT), images taken using magnetic resonance imaging (MM), or the like. In some implementations, disease detection is accomplished by feature detection. A DD model can make a determination that a disease is present after detecting certain features in the input image. A DD model can make a determination that a disease is present using a number of different models such as neural network models, SVM models, Decision Trees, Random Forests, Naïve Bayes models, among others. The determination that a disease is present can be made using singular aforementioned models or a combination of them.

With reference to FIG. 2, electronics (or electronic processing circuitry) 210 can include one or more controllers or processors configured to use one or more DD models to analyze one or more images to determine if the image is of sufficient quality or not.

Decision Maker

Figure 3:
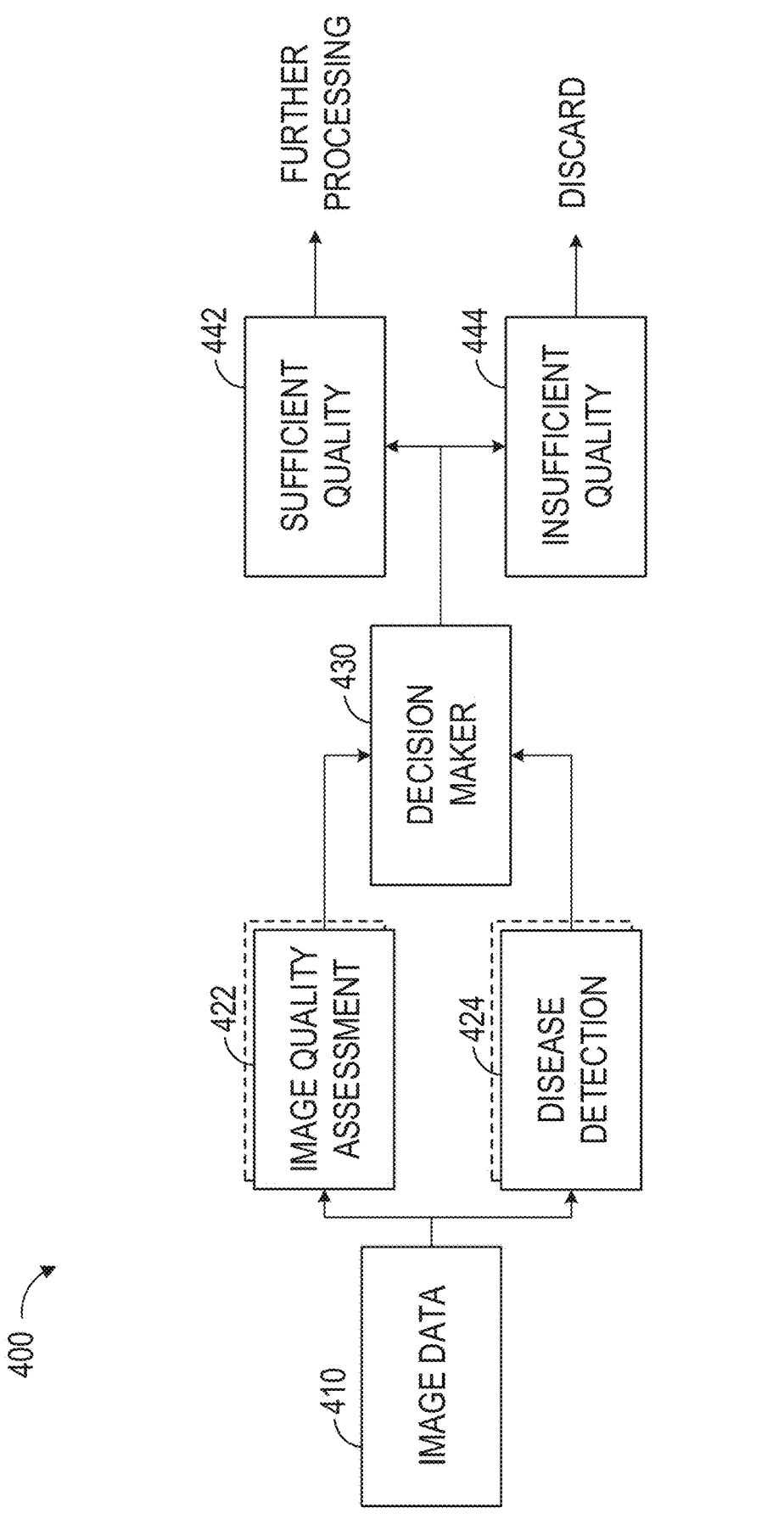
FIG. 3 illustrates an example image quality assessment process.

FIG. 3 illustrates an example image quality assessment or determination process 400. The process 400 can be implemented by the retina camera 100, such as by the electronics 210. The process 400 can assess the quality of image data 410, which can be collected as described herein. Image data can be one or more images and/or video data stored in the storage 224. For example, image data can be an image of a retina (or another body part).

The process 400 can provide the image data 410 to an image quality assessment component 422 (or IQA) and a disease detection component 424 (or DD). In some implementations, the image quality assessment component 422 is a image quality assessment module. In some implementations, the disease detection component 424 is a disease detection module. The image quality assessment component 422 can use an IQA model to assess the quality of the image. The disease detection component 424 can use a DD model to detect whether the image is indicative of a disease or biomarker. The image quality assessment component 422 and the disease detection component 424 can process the image data 410 in parallel or sequentially.

For example, the process 400 can process the images through the IQA model in the image quality assessment component 422 and store the output in memory (such as, in the storage 224) prior to processing the images with the DD model in the disease detection component 424. As another example, the process 400 can process the images through the DD model in the disease detection component 424 and storing the output in memory prior to processing the images with IQA model in the image quality assessment component 422. After the images are processed by both the IQA model and the DD model, the output of the image quality assessment component 422 and the disease detection component 424 are provided as inputs to a decision maker component 430. In some implementations, the decision maker component 430 (or decision maker) is a decision maker module.

The output of the image quality assessment component 422 and the output of the disease detection component 424 can be used to create the output of the decision maker component 430. If the output of the decision maker component 430 is determined to be of sufficient quality 442, the output of the decision maker component 430 can be further processed or used to make a decision. Further processing can include, for example, providing an indication of presence (or absence) of a disease. If the output of the decision maker component 430 is determined to be of insufficient quality 444, the image can be discarded, unused, or used for alternate processing. The image quality determination process 400 can obtain new image data or process a different image that has been previously obtained.

The decision maker component 430 can use the outputs of the disease detection component 424 and the image quality assessment component 422 to ensure optimal system performance and reduce the need to retake images or prolong a medical imaging procedure. The overall purpose can be to diagnose a particular disease. To that effect, the outputs of the image quality assessment component 422 and the disease detection component 424 can be used together to diagnose a particular disease. The image quality assessment component 422 can use an image quality assessment process to assess the quality of input images. The disease detection component 424 can use a disease detection process to classify and diagnose input images to determine if a disease is detected. By working in a symbiotic relationship and combining the outputs of the image quality assessment component 422 and the disease detection component 424 together, an optimum result can be achieved that allows for the highest accuracy.

Determinations made by the image quality assessment component 422 and disease detection component 424 can be combined as described herein. The combined analysis of disease detection outputs and image quality assessment outputs allows for more accurate evaluation of medical images.

In order to determine sufficient quality 442, the decision maker component 430 may need to determine the probability that the image is of sufficient quality and/or be sufficiently confident that the image is of sufficient quality for it to successfully detect the presence or absence of disease. Determination of sufficient or insufficient quality can be made by determining a quality score of the image based on the outputs of the image quality assessment component 422 and the disease detection component 424. The outputs of the image quality assessment component 422 and the disease detection component 424 can be combined (for example, linearly combined by methods such as averaged or weighted averaged or non-linearly combined) to determine the quality score (for example, by the decision maker component 430).

The quality score can be compared to a quality threshold (for example, by the decision maker component 430) to determine whether the quality is sufficient or insufficient. In some implementations, a quality threshold can be determined by the dataset used to train a model. In some implementations, the quality threshold may be determined automatically by using a dataset having the same distribution as the training set. In some implementations, a quality threshold can be determined without the need for a specific threshold to be chosen by a person. In some implementations, a quality threshold can be set by a person.

In one example, a quality threshold of 0.5 can be determined. If the weighted average of the quality scores is above 0.5, then the decision maker component 430 deems the image to be of sufficient quality. This threshold can be fit based on the training data to maximize system sensitivity and specificity, for example. The outputs of the image quality assessment component 422 and the disease detection component 424 can also be combined in a combinatorial manner, where the decision maker component 430 looks at a finite number of cases to determine the quality. Advantageously, the process 400 using a decision maker component 430 can provide for more accurate image quality analysis, lead to faster medical imaging procedures, and reduce the need to retake images or entirely re-perform medical imaging procedures. Real-time imaging diagnostics devices or systems can be easier to use, since a device can provide more accurate and instantaneous feedback to the user regarding the quality of the images and/or video being captured. The decision maker component 430 can be more robust and faster than other systems by reducing the need to retake images while maintaining performance of the diagnostic system.

ML/DL disease detection algorithms can use a large number of parameters to determine the presence or absence of a disease. IQA models may identify images as sufficient quality, but the images may not have the right characteristics for optimal disease detection by a DD model. This can result because the IQA model may be simpler or uses fewer parameters. For example, the IQA method may identify an image as sufficient quality, but the disease detection algorithm may indicate low probability and/or low confidence in the detection of a disease because the image is not of sufficient quality based on the parameters the disease detection algorithm is using for analysis or the image is greatly out of distribution of the training data on which the classification algorithms were developed.

ML/DL disease detection algorithms can also have a high degree of false confidence in their prediction, which can lead to a large number of false positives and false negatives. For example, the disease detection algorithm may assign the presence of disease in an unrelated image (for example, of an eyelid), while the IQA model may assign a high confidence that the image is of low quality and/or a low probability that the image is of sufficient quality. In these cases, the IQA method can override the disease detection algorithm, and the image can be retaken.

The following paragraphs provide an example of using the process 400 for assessing presence of a disease, such as a diabetic retinopathy (DR).

Figure 4:
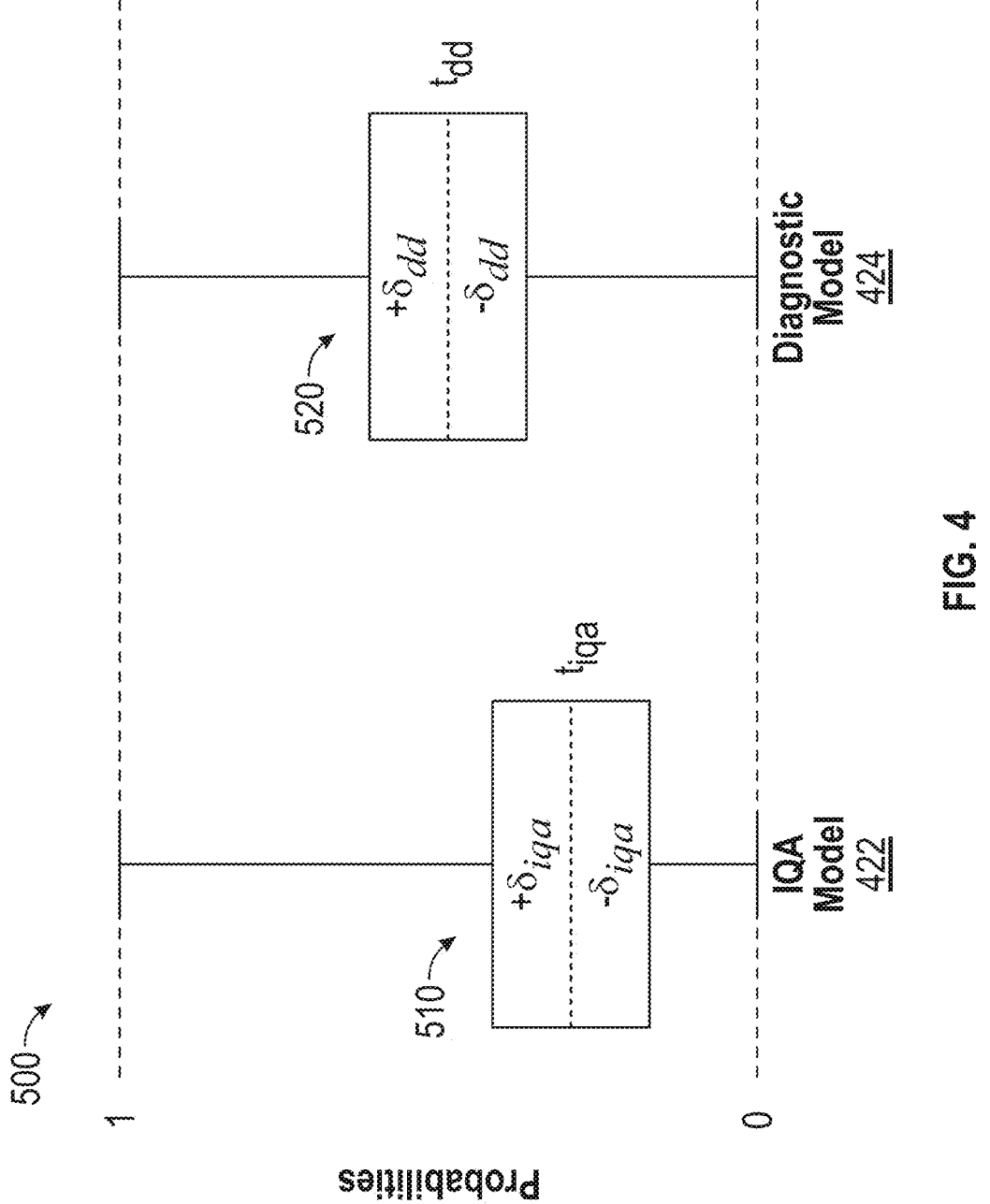
FIG. 4 illustrates example threshold ranges for image quality assessment.

With reference to FIG. 4, given an image I, a DD model (or classifier) can output a predicted probability of disease presence, $p_{DD}$ and assign the label '1' (contains DR) if $p_{DD} \geq t_{DD}$, where $t_{DD}$ is a given threshold for detection of DR, or the label '0' (does not contain DR) if $p_{DD} < t_{DD}$, as seen in equation 1:

$$D_i = \begin{cases} 1 & \text{if } p_{DD} \geq t_{DD} \\ 0 & \text{if } p_{DD} < t_{DD} \end{cases} \quad (1)$$

with $D_1$ being the classification output of the DD model, $p_{DD}$ being the DD model probability for image i, and $t_{DD}$ the determined threshold. The determined threshold can be determined by training or validation data, selected by the model's designer, or the like. The determined threshold can be obtained through various choices determined by the model's designer through the use of various metrics, such as sentitivity, specificity, precision, or the like. The determined threshold can be optimized for the performance of the DD model.

The same image I can be an input to an IQA model, which can output a predicted probability that the image is of sufficient quality, $p_{IQA}$, and assign the label '1' (the image is of sufficient quality) if $p_{IQA} \geq t_{IQA}$, where $t_{IQA}$ is a given threshold for an image being of sufficient quality, or the label '0' (the image is not of sufficient quality) if $p_{IQA} < t_{IQA}$, as seen in equation 1:

$$Q_i = \begin{cases} 1 & \text{if } p_{IQA} \geq t_{IQA} \\ 0 & \text{if } p_{IQA} < t_{IQA} \end{cases} \quad (2)$$

with $Q_i$ being the image quality output of the IQA model, $p_{IQA}$ being the IQA model probability that image i is of sufficient quality, and $t_{IQA}$ the determined threshold. The determined threshold can be determined by training data, selected by the model's designer, or the like. The determined threshold can be obtained through various choices determined by the model's designer through the use of various metrics, such as sentitivity, specificity, precision, or the like. The determined threshold can be optimized for the performance of the IQA model.

In one example, the process 400 could be used to classify whether X-ray images of lungs show signs of Covid-19. In this example system, a diagnostics system could consist of an IQA and a DD model. In such a system, once trained, each of the models would have thresholds to output binary probability predictions. The probability of these models, after being passed through the threshold, would indicate either 0 or 1. For the IQA, an output of 0 can reflect a poor image for the IQA and 1 can indicate a good image for the IQA. For the DD, an output of 0 can indicate no signs of Covid-19, and an output of 1 can indicate signs of Covid-19. In order to optimize the performance of the system as a whole, the output probabilities of both models, along with the chosen thresholds for each model would be taken into account, and optimized using, for instance, a single optimization function. The objects of the optimization would be a threshold range for each of the models respectively. This threshold range can be a confidence window or a confidence interval, but can be used to describe either a range around a probability threshold or a range around a confidence threshold.

Both the IQA and DD model can also produce an output $c_{IQA}$ and $c_{DD}$, respectively, which are the confidence in the correctness of the estimate $p_{IQA}$ and $p_{DD}$, respectively. Confidence estimates may be obtained by model calibration methods, such as Platt scaling, among other techniques. As such, $p_{IQA}$, $p_{DD}$ may or may not be equal to $c_{IQA}$, $c_{DD}$. Models, such as deep neural network architectures, can output predictions $p_{DD}$ that are greater than $c_{IQA}$, $c_{DD}$, indicating that the network is overconfident compared to the true confidence of a prediction. Furthermore, the DD model may output large values of $p_{DD}$ even in the cases where an input image contains many artifacts, or may not even be of the correct type of image. For example, although the DD model is trained on retinas, the model can have high confidence in its prediction even if the input image is an eyelid. $c_{IQA}$, $c_{DD}$ can also be plotted on a graph similar to FIG. 4 wherein the y-axis is confidence (instead of probability) and can range across any appropriate confidence range (instead of of 0 to 1).

Depending on the task at hand and the implementation of the algorithm, once trained, an IQA or DD model performance can be linked to a determined threshold. For example, the determined threshold can be a binary classifier. The chosen threshold, t, in general can be chosen such that the model generates the best performance. When analyzing a system as a whole, the individual performance of each ML/DL model (for example, an IQA model and a DD model) may differ from the overall system performance. This may be particularly relevant in sequential approaches, where the input of one model is the output of another and is therefore impacted by the previous model's performance. Therefore, in order to achieve the best system performance, both models can be taken into account and the system be optimized as a whole.

The process 400 represents a holistic approach to image quality determination, where both the IQA model and DD model can impact each other's decision and predictions. The level of involvement in either module can be determined by the system designer, and can be set mathematically, for example by maximizing one or more metrics. Example metrics can include whole system sensitivity and specificity.

The confidence of a DD or an IQA model's output probability can either be defined in a rigorous mathematical manner or can be estimated such as by using a surrogate measure. When the confidence of a model's output probability is defined in a rigorous mathematical manner, the output of the neural network can output a predictive distribution or a single point prediction. In some implementations, the output can be an output prediction uncertainty, for example by using a Baysian Neural Network.

With reference to FIG. 4, the threshold range can relate to some distance away from a threshold, t where the model output can be a probability between and inclusive of 0 and 1. The threshold range can be defined as $\omega=[t-\delta, t+\delta]$, where $\omega$ represents the threshold range, where $\delta$ the distance from the threshold t, where $t+\delta$ represents the upper bound, and where $t-\delta$ represents the lower bound. In FIG. 4, examples of a threshold range 510 of the IQA model (such as, the image quality assessment component 422) and a threshold range 520 of the DD model (such as, the disease detection component 424) are shown. The threshold t, the threshold range $\omega$, and the distance from the threshold $\delta$, for each model can be different. As the individual model thresholds are fixed, the optimization of the system as a whole consists of obtaining the best threshold ranges for both the IQA model and the DD model, by optimizing over the joint performance of the models such that the loss function being optimized over is the following:

$$\mathcal{L}_{(\delta_{iqa}, \delta_{dd})} = -(M(\mathcal{J}, \mathcal{T}; \delta_{iqa}) + (1 - M(\mathcal{G}, \mathcal{T}; \delta_{dd}))) \qquad (2)$$

where $\mathcal{L}$ represents the loss function to be minimized, $\delta_{iqa}$ is the distance away from the threshold of the IQA, $\delta_{dd}$ is the distance away from the threshold of the DD, M, is a metric of choice, $\mathcal{J}$ represents the diagnostic output of the images that have been let through the IQA, $\mathcal{T}$ the ground truth diagnostic of the images, and $\mathcal{G}$ represents the diagnostic output of the images that have not been let through the IQA. Example metrics of choice can include accuracy and binary accuracy. An example ground truth diagnostic of the images can be the assessment that some images are indicative of a disease or biomarker, and other images are not indicative of the same disease or biomarker. In this example, where there are two models making up the system, nine possible cases can exist, and can be seen with reference to FIG. 4.

1. The IQA probability falls over $t+\delta$ and the DD probability falls over $t+\delta$
2. The IQA probability falls over $t+\delta$ and the DD probability falls under $t-\delta$
3. The IQA probability falls over $t+\delta$ and the DD probability falls inside $\omega$
4. The IQA probability falls under $t-\delta$ and the DD probability falls over $t+\delta$
5. The IQA probability falls under $t-\delta$ and the DD probability falls under $t-\delta$
6. The IQA probability falls under $t-\delta$ and the DD probability falls inside $\omega$
7. The IQA probability falls inside $\omega$ and the DD probability falls inside $\omega$
8. The IQA probability falls inside $\omega$ and the DD probability falls over $t+\delta$
9. The IQA probability falls inside $\omega$ and the DD probability falls under $t-\delta$ The loss function $\mathcal{L}$ above can take all nine possible cases into account in order to generate the best threshold ranges for both the IQA and DD models, such the system as a whole can generate the best performance for the overall system while reducing the need to retake images as much as possible.

The system designer or manager can design the system or the decision maker component 430 to output different results for each of the nine cases above. The output from the decision maker component 430 can be indicative of a quality score's relationship to a quality threshold which then can be interpreted by the system to lead to a conclusion or action. For example, the output of the decision maker component 430 may be a binary output of 1 or 0 (with "1" indicating sufficient image quality and "0" indicating insufficient image quality). In some implementations, the binary outputs can be determined by one or more datasets used to train one or more models used in the system. In some implementations, the binary outputs can be determined without the need for binary outputs to be chosen by a person. In some implementations, the binary outputs can be set by a person. An example of binary outputs is shown in the below Table 1 for the nine cases described above.

TABLE 1

| Example Binary Outputs of the Decision Maker Component 430 of FIG. 3 | | | |
| --- | --- | --- | --- |
| | IQA probability falls over t + δ | IQA probability falls inside ω | IQA probability falls under t − δ |
| DD probability falls over t + δ | 1 | 1 | 1 |
| DD probability falls inside ω | 0 | 0 | 0 |
| DD probability falls under t − δ | 1 | 0 | 1 |

The decision maker component 430 can then use the binary outputs to determine the appropriate distance from the threshold $\delta$ for each model and thus the appropriate threshold range $\omega$ for each model (for example, for the IQA model and the DD model referenced in FIG. 4) in order to optimize the overall system. This can create distances from the threshold δ, and threshold ranges ω for each model represented in FIG. 4.

With reference to the example system in FIG. 3, the binary output can then be used by the system to determine that in the case of 1, the image is of sufficient quality 442 or the image is of insufficient quality 444. In the example system of FIG. 3, an image that is of sufficient quality 442 may be further processed by a machine or person, which can lead to a clinical or other decision. In the example system of FIG. 3, an image that is of insufficient quality 444 can be discarded or unused. This can lead to a system output that another image must be taken or instruct a person to take another image.

The binary outputs of the decision maker component 430 as seen in Table 1 demonstrate an example optimization achieved by the system. In the case where the IQA probability falls inside ω and the DD probability falls over t+δ the system is designed to determine that the image is of sufficient quality for further processing and/or determination that the disease is present (assuming that the DD probability falls over t+δ indicates the presence of the disease). If the output of the IQA model was sequentially fed into the DD model, the system may have determined that the image quality of the input image to the IQA was insufficient and discarded the image before the DD model could determine that the input image was sufficient to determine the presence of the disease. With reference to FIG. 4, these images would fall in the IQA probably range of [t−δ, t] in the threshold range ω. This is an example where although the image quality does not satisfy its threshold, the DD model overrides the IQA, setting the quality score to satisfy the quality threshold irrespective of the image quality. In such an example, the choice of δ and subsequent threshold range ω, would take this decision into account such that by having the DD model override the choice of the IQA, the performance of the system as a whole is optimum.

Another example of binary outputs is shown in the below Table 2 for the nine cases described above.

TABLE 2

| Example Binary Outputs of the Decision Maker Component 430 of FIG. 3 | | | |
|---|---|---|---|
| | IQA probability falls over t + δ | IQA probability falls inside ω | IQA probability falls under t − δ |
| DD probability falls over t + δ | 1 | 1 | 1 |
| DD probability falls inside ω | 1 | 0 | 0 |
| DD probability falls under t − δ | 1 | 0 | 1 |

The binary outputs of Table 2 are different from Table 1. With reference to FIG. 3, it can be seen that this set of outputs from the decision maker component 430 is more permissive in determining that an image is of sufficient quality, assuming 1 means the image is of sufficient quality and 0 means the image is of insufficient quality. The decision maker component 430 used in Table 2 may be more permissive in determining an image is of sufficient quality as compared to the decision maker used in Table 1 for many reasons. Example reasons for the difference between the binary outputs of the decision maker components 430 of Table 1 and Table 2 may include that the type of image is different (for example, an MRI image. CT image, or a photograph), the part of the body that is imaged is different (for example, the retina of the eye, or the lungs, or the heart), the clinical decisions that may be required based on diagnosis are different, or the risks associated with misdiagnosis are different. Differences between the binary outputs of the decision maker components 430 of Table 1 and Table 2 can include any clinical, therapeutic, diagnostic, or medical reasons, or any system, hardware, software, probabilistic, confidence, manufacturing of device/system reasons.

The binary outputs of the decision maker component 430 as seen in Table 2 demonstrate another example optimization achieved by the system as compared to Table 1. In the case where the IQA probability falls over t+δ and the DD probability falls inside ω, the system is designed to determine that the image is of sufficient quality for further processing and/or determination that the disease is present or not present (assuming that if the DD probability falls under t indicates that the disease is not present and if the DD probably falls over t indicates that the disease is present). If the output of the IQA model was sequentially fed into the DD model, the system may have determined that the probability output of the DD model was insufficient to actually diagnose the presence/lack of presence of the disease. This is an example where although the certainty measure of the DD model does not satisfy its threshold, the IQA model overrides the DD model, setting the quality score to satisfy the quality threshold irrespective of the certainty measure of the DD model, wherein the certainty measure is either a probability or a confidence score by the DD model that the disease is present or not present.

Such a system as a whole can generate the best performance for the overall system while reducing the need to retake images as much as possible. For example, in such a system, an IQA model that has an accuracy of 70% and a DD model that has an accuracy 95% can increase each other's respective accuracies through the optimization achieved by the decision maker component 430. For example, the IQA model can have an increased accuracy of 80% and the DD model can have an increased accuracy of 96%.

In some implementations, the confidence or predicted output probability of the DD model can be used to override the IQA. For instance, IQA could have a low probability indicating that the image is of insufficient quality (such as, about 60% or less), but DD model can be high probability that the disease is present (such as, about 75% or more). In such case, the determination by the DD model can override the IQA model, and the image can be determined to be of sufficient quality for further processing or use in diagnosis or the like. The system can trust the DD model, despite the determination by the IQA. Examples where it can be useful for the DD model confidence or predicted output probability to override the IQA module can include: 1) the IQA module may be trained on a limited dataset, 2) the IQA module may not have reliable performance, or 3) the IQA module may be unable to distinguish nuanced cases. Alternatively or additionally, the DD model can be a black box that uses imaging features that are missed by the IQA module. The degree of confidence by the disease detection algorithm can be optimized and set based on the image quality assessment module used.

In some implementations, the IQA module may override the DD model and prompt the system to acquire a new image (or use a different image). In such a system, the DD model may output confidence in its prediction in addition to probability of the disease being detected or not. For example, the DD model may output 50% confidence of presence of disease, while the IQA module may output 10% probability indicating an image is a poor quality image. In this example, the system can prompt the user to acquire a new image (or use a different image) to minimize the risk of a false positive detection or a false negative. In this approach, the IQA can be used to minimize both epistemic and aleatoric uncertainty. Epistemic uncertainty can be minimized by rejecting images that the DD model has never seen before. Aleatoric uncertainty can be reduced by rejecting images of poor quality.

In some implementations, the IQA module can also output confidence in its prediction. In some implementations, both the IQA module and the DD model outputs can have low confidence, prompting the system to acquire a new image. If multiple images are acquired with both the DD model and IQA having low confidence, the system may choose to simply trust the DD model prediction, or request a manual intervention. In some implementations, where there is a low cost of outputting a false positive result, the decision maker component 430 may place a lower weight on the confidence of the DD model output predicting the presence of disease. An example where there is low cost of outputting a false positive is when positive disease diagnosis leads to a specialist referral. In cases where there is a low cost of outputting a false positive, the decision maker component 430 can output sufficient quality when both the IQA and DD model have low confidence, but the DD model predicts the presence of disease. In this example, the decision maker component 430 would take into account the output confidence of the models as well as their output probabilities.

For example, if the image quality assessment component 422 deems the image to be of poor quality with a high confidence, and disease detection component 424 determines the image has the presence of disease with low confidence, then the decision maker component 430 can determine the image to be of insufficient quality. This can depend on the inherent choices made to optimize the system as a whole. The decision maker component 430 is specifically optimized such that the joint outputs of the IQA and DD model are taken into account to obtain the best system performance as a whole. That means that in some cases even if the quality of the image is poor but the DD output is true, if overall, using significant data, the overall system performance is good, then the parameters of the decision maker component 430 will be updated as such and reflected on the "confidence" of the individual models.

In some implementations, the system is designed such that if the IQA is slightly confident (or not confident) that the image is of poor quality and the DD model is very confident that it has detected the presence or absence of disease, the decision maker component 430 will determine the image is of sufficient quality. As such, the DD model overrides the IQA.

In some implementations, the system is designed such that if the IQA is very confident that the image is of poor quality and the DD model is slightly confident (or not confident) that it has detected the presence or absence of disease, the decision maker component 430 will determine the image is of insufficient quality and can retake the image or output an indication that the image should be retaken. As such, the IQA overrides the DD model.

In some implementations, both the DD model is very confident that it has detected the presence or absence of disease and the IQA is very confident that the image is of poor quality, the decision maker component 430 will determine the image is of sufficient quality. As such, the DD model overrides the IQA. Alternatively, in this same scenario, the IQA can override the DD model such that the decision maker component 430 outputs that the image is of insufficient quality.

In some implementations, when the system determines an image is of insufficient quality, it may automatically retake an image. In other implementations, the system may indicate to the user to manually retake the image.

In some implementations, multiple IQA modules, components, or models can be combined with multiple DD modules, components, or models such that the decision maker component 430 has input from the multiple IQA modules, components, or models and multiple DD modules, components, or models. In some implementations, the decision maker component 430 can include multiple disease detection components 424 and/or multiple image quality assessment components 422. In some implementations, one set of a disease detection component 424 and an image quality assessment component 422 can be trained on one imaging modality while another set of a disease detection component 424 and an image quality assessment component 422 can be trained on another imaging modality. The decision maker component 430 can use the outputs of multiple disease detection components 424 and/or multiple image quality assessment components 422 to determine the output of the decision maker component 430. Where a decision maker component 430 uses the outputs of N components (or the decision maker component 430 has N inputs), the decision maker component 430 can have outputs for $3^N$ cases because each component can output a probability or confidence that is either 1) below the threshold range, 2) above the threshold range, or 3) within the threshold range.

For example, a decision maker component 430 could have four inputs: an image quality assessment component 422 for an Mill image, a disease detection component 424 for an Mill image, an image quality assessment component 422 for a CT image, and a disease detection component 424 for a CT image. Such a decision maker may need to have outputs for 81 cases. In such an example, a table (similar to Table 1 and Table 2) representing the outputs of the decision maker would contain 81 cells. The decision maker component 430 can then use the outputs to determine the appropriate distance from the threshold δ for each model or component and thus the appropriate threshold range ω for each model or component in order to optimize the overall system. Thus, the system can create thresholds t, distances from the threshold δ, and threshold ranges ω for each model.

In another example, a decision maker component 430 could have four inputs: an image quality assessment component 422 for the probability that an image is of sufficient quality, an image quality assessment component 422 for the confidence in the probability that the image is of sufficient quality, a disease detection component 424 for the probability that the disease is detected, and a disease detection component 424 for the confidence in the probability that the disease is detected.

In some implementations, multiple levels of IQA methods can be combined with the DD model. The IQA methods can increase in level of granularity in predicting image quality. For example, the first layer may filter for the presence or absence of the desired anatomy. The second layer may filter for sharpness. The system can then assign varying degrees of importance to each of these layers when combined with the DD model to arrive at a prediction.

In some implementations, the system is a probabilistic approach to disease detection. The decision maker component 430 can use one or many thresholds to output a binary score, for example '1': disease present, or '0': disease absent. In some implementations, the system can output a categorical score, with a fixed number of levels to indicate disease severity. This system can output a combination of disease severity level, a degree of confidence in the prediction, where the degree of confidence is derived from the confidence of the DD model and the IQA. This can reduce the number of false positives and negatives, and provide a more explainable output for humans. In some implementations, the decision maker component 430 can output a score that has 3, 4, 5, or more kinds of outputs which can correlate to an equal number of sets of different actions, decisions, or the like being made by the system.

In some implementations, the output(s) of the disease detection component 424 can be used by the image quality assessment component 422. In some implementations, the probability of the presence of disease may be incorporated into the image quality assessment. In some implementations, the confidence in the probability of the presence of disease may be incorporated into the image quality assessment. In some implementations, the probability and confidence may both be incorporated into the image quality assessment.

In some cases, the disease detection component 424 (or another similar component that may be positioned upstream) may detect presence of a feature in an image. For example, for a retinal image this can be presence of a retinal disc. As another example, for colonoscopy this can be presence of a polyps in a particular location of the colon. If the process 400 determines that the image is of sufficient quality based on presence of the feature, the image can be further processed for disease detection. This approach can be advantageous for application where in addition to high image quality, it is important that an image captures a particular anatomical feature.

In some implementations, the system may include an IQA algorithm that uses thresholds, ranges, and/or limits for the various characteristics used to evaluate image quality. For example, the decision maker component 430 may use one criterion (e.g., a threshold) for the confidence of the disease detection component 424 and another criterion (e.g., a threshold or range) for image brightness that must both be met for the image to be identified as sufficient quality.

In some implementations, the output(s) of the IQA can be input(s) for the DD model. In some implementations, the probability of a poor quality image can be an input into the DD model. In some implementations, the confidence in the probability of a poor quality image can be an input into the DD model. In some implementations, both the probability and confidence can be inputs into the DD model.

In some implementations, both the output(s) of the IQA and the DD model may be combined to produce the desired output, such as presence or absence of disease, with additional measure of system-level confidence in the prediction. For example, the system may predict the presence of disease and output to the user the degree of confidence in the prediction by using the confidence in the probability of the outputs of the IQA and the DD model. In some implementations, the confidence of the output of the IQA can affect the confidence of the output of the DD model. For example, the system-level confidence of a prediction that a person has DR is 75% confidence, wherein the 75% confidence is based on how good the image quality is and how confident the DD model is in the prediction of the presence of DR. A decision-tree algorithm can be developed to use the outputs of the DD model and the IQA module on whether to trust or retake an acquired image.

In some implementations, a parametric model using the outputs can be fitted to the dataset. A parametric model can be any model that captures all the information about its predictions within a finite set of parameters. Similarly, in some implementations, a non-parametric model could also be used. In some implementations, a discrete set of windows of output values can be used to produce regions of varying trust in the acquired image.

In some implementations, the output(s) of the DD model may be combined with IQA methods to provide a combined image quality evaluation. These image quality assessment methods may include, but are not limited to, brightness limits, sharpness evaluation, image illumination, the presence of image features, and histogram-based comparisons.

In some implementations, the IQA method implemented by the image quality assessment component 422 can be semi-autonomous, for example by incorporating user input. The proposed system can combine outputs of the DD model and IQA, and in cases of high uncertainty, the system can ask the user to approve or disapprove the acquired image.

In some implementations, the system can analyze video by decomposing the video into a series of images. In some implementations, the system can analyze every image of the video. In some implementations, the system can analyze one out of every two images. In some implementations, the system can analyze one out of every X images, where X can be any integer N, such as three, four, five, six, ten, fifteen, twenty, thirty, fifty, hundred, two hundred, three hundred, or one thousand, or the like. With reference to the process 400 of FIG. 4, the system can analyze only those images that are of sufficient quality and discard images that are of insufficient quality.

In some implementations, the disease detection component 424 and image quality assessment component 422 can be trained to be used in retinal imaging. However, the disease detection component 424 and the image quality assessment component 422 can be trained to be used for a multitude of imaging modalities, including 2D/3D photography, optical coherence tomography (OCT), ultrasound, X-Ray, coherence tomography (CT), magnetic resonance imaging (MRI), positron emission tomography (PET), and any other imaging modality where images and/or video outputs are evaluated for quality prior to analysis.

Other Variations

Any of the thresholds described herein can be static or dynamic.

Although the foregoing provides one or more examples of a retina camera, the disclosed systems, devices, and methods are not limited to retina cameras, but can be extended to any diagnostics device, such as an otoscope, dermatology scope, X-Ray system, MM system, CT system, or the like. Although the foregoing provides one or more examples of a portable medical diagnostics device, the approaches disclosed herein can be utilized by non-portable (such as, table top) diagnostics devices.

Although the forgoing provides one or more examples of images including retinal images, the disclosed systems, devices, and methods are not so limited, but can be extended to any image, especially images used for medical diagnostics, such as X-Ray images, computed tomography (CT) images, non-contrast head CT images (NCHCT), images taken using magnetic resonance imaging (MM), or the like.

The systems, devices, and methods can be useful for portable X-Ray applications. Portable X-Ray systems can be used for bed-bound patients or patients in critical condition. Imaging for patients who cannot be moved can be difficult. Thus a portable scan can be performed and even if the result is a poor quality image, the system may be able to detect a patient condition (for example, a condition such as a large effusion, a pneumothorax, anintraparenchymal pathology, or the like). This can reduce the need for patients to be moved to have the difficult imaging procedure performed, which can decrease imaging time, radiation exposure, and patient-provider frustration.

The systems, devices, and methods can be useful for NCHCT images. For example, a patient with acute intracranial bleed can have a non-contrast head CT performed where the patient moves, seizes, or is removed from table during the procedure, which leads to significant image artifacts or portions of the scan missing. Such images can be assessed as poor quality by an IQA, but a large epidural hematoma can be detected. This can allow a surgical team to begin treating or acting immediately. In this example, the image doesn't need to be of great quality because the clinical question that led to the decision to obtain the image (e.g. is there a bleed?) was sufficiently answered.

The systems, devices, and methods can be useful for images obtained by use of MRI. For example, the image obtained via MRI can have a significant motion artifact, but the disclosed systems, devices, or methods are able to make out a diagnosis, lesion, pathology, injury, or the like. Obtaining another image is unlikely to change treatment or diagnosis because the image was of sufficient quality to reveal the suspected underlying pathology/lesion/injury to allow initiation of treatment. Images obtained via MM can be expensive and can be of limited availability. The systems, devices, and methods disclosed can be useful to reduce the need for repeat imaging reducing monetary costs, human capital, and patient/healthcare worker time.

Any of the transmission of data described herein can be performed securely. For example, one or more of encryption, https protocol, secure VPN connection, error checking, confirmation of delivery, or the like can be utilized.

Although the foregoing provides one or more examples of live image or video analysis on-board, disclosed systems, devices, and methods are not so limited and can be utilized by cloud-based systems, particularly in situations where reliable network connectivity is available.

Depending on the implementation, certain acts, events, or functions of any of the processes or algorithms described herein can be performed in a different sequence, can be added, merged, or left out altogether (e.g., not all described operations or events are necessary for the practice of the algorithm). Moreover, in certain implementations, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the implementations disclosed herein can be implemented as electronic hardware, or combinations of electronic hardware and computer software. To clearly illustrate this interchangeability of hardware and software, various illustrative components, blocks, modules, and steps have been described above generally in terms of their functionality. Whether such functionality is implemented as hardware, or as software that runs on hardware, depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the implementations disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electronic circuitry configured to process computer-executable instructions. In another implementation, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the implementations disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An example storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain implementations include, while other implementations do not include, certain features, elements and/or steps. Thus, such conditional language is not generally intended to imply that features, elements and/or steps are in any way required for one or more implementations or that one or more implementations necessarily include logic for deciding, with or without other input or prompting, whether these features, elements and/or steps are included or are to be performed in any particular implementation. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain implementations require at least one of X, at least one of Y, or at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

While the above detailed description has shown, described, and pointed out novel features as applied to various implementations, it can be understood that various omissions, substitutions, and changes in the form and details of the devices or algorithms illustrated can be made without departing from the spirit of the disclosure. As can be recognized, certain implementations described herein can be embodied within a form that does not provide all of the features and benefits set forth herein, as some features can be used or practiced separately from others. The scope of certain implementations disclosed herein is indicated by the appended claims rather than by the foregoing description. All changes which come within the meaning and range of equivalency of the claims are to be embraced within their scope.

What is claimed is:

1. A retina camera comprising:
a housing;
a light source supported by the housing, the light source configured to irradiate an eye of a patient with light;
imaging optics supported by the housing, the imaging optics configured to receive light reflected by the eye;
an image detector array supported by the housing, the image detector array configured to receive light from the imaging optics and to sense the received light; and
an electronic processing circuitry supported by the housing, the electronic processing circuitry configured to:
generate at least one image of the eye based on signals received from the image detector array;
assess an image quality of the at least one image;
process the at least one image with a machine learning model to determine a certainty measure indicative of a presence of at least one disease from a plurality of diseases that the machine learning model has been trained to identify;
determine a quality score for the at least one image based on the image quality of the at least one image and the certainty measure indicative of the presence of the at least one disease, wherein determining the quality score comprises:
in response to the image quality not satisfying an image quality threshold indicative of sufficient image quality for disease detection, setting the quality score to a value that does not satisfy a quality threshold irrespective of the certainty measure satisfying a first certainty threshold indicative of sufficient likelihood that the at least one disease is present, and
in response to the certainty measure satisfying a second certainty threshold indicative of higher likelihood that the at least one disease is present than the first certainty threshold, setting the quality score to a value that satisfies the quality threshold irrespective of the image quality not satisfying the image quality threshold indicative of sufficient image quality for disease detection;
in response to a determination that the quality score does not satisfy the quality threshold, discard the at least one image; and
in response to a determination that the quality score satisfies the quality threshold, provide an indication of the presence of the at least one disease.

2. The retina camera of claim 1, wherein the electronic processing circuitry is configured to assess the image quality of the at least one image with another machine learning model different from the machine learning model.

3. The retina camera of claim 1, further comprising a display at least partially supported by the housing, wherein the electronic processing circuitry is further configured to provide the indication of the presence of the at least one disease on the display.

4. The retina camera of claim 1, wherein discarding the at least one image causes the at least one image to be retaken.

5. The retina camera of claim 1, wherein the image quality is assessed based on at least one of a probability or a confidence score.

6. The retina camera of claim 1, wherein the certainty measure is based on at least one of a probability generated by the machine learning model or a confidence score generated by the machine learning model.

7. The retina camera of claim 1, wherein the at least one image comprises a plurality of images determined from a video of the eye, and wherein discarding the at least one image causes use of another image from the plurality of images for detecting the presence of the at least one disease.

8. The retina camera of claim 1, wherein the electronic processing circuitry is configured to determine the quality score for the at least one image by:
in response to the certainty measure for the presence of the at least one disease not satisfying a third certainty threshold indicative of insufficient likelihood that the at least one disease is present, setting the quality score to a value that does not satisfy the quality threshold irrespective of the image quality satisfying the image quality threshold.

9. The retina camera of claim 1, wherein the electronic processing circuitry is configured to:
determine a confidence of the presence of the at least one disease based on a confidence score generated by the machine learning model and a confidence score generated by another machine learning model configured to assess the image quality of the at least one image; and
output the confidence of the presence of the at least one disease along with the indication of the presence of the at least one disease.

10. A medical diagnostics system comprising:
an energy source configured to direct electromagnetic waves toward a body part of a patient;
a detector configured to sense a response of the body part to the electromagnetic waves; and an electronic processing circuitry configured to:

generate at least one representation of the body part based on the response sensed by the detector;

assess a quality of the at least one representation;

process the at least one representation with a machine learning model to determine a certainty measure indicative of a presence of at least one disease from a plurality of diseases that the machine learning model has been trained to identify;

determine a quality score for the at least one representation based on the quality of the at least one representation and the certainty measure indicative of the presence of the at least one disease, wherein determining the quality score comprises:

in response to the quality of the at least one representation not satisfying a representation quality threshold indicative of sufficient quality for disease detection, setting the quality score to a value that does not satisfy a quality threshold irrespective of the certainty measure satisfying a first certainty threshold indicative of sufficient likelihood that the at least one disease is present, and in response to the certainty measure satisfying a second certainty threshold indicative of higher likelihood that the at least one disease is present than the first certainty threshold, setting the quality score to a value that satisfies the quality threshold irrespective of the quality of the at least one representation not satisfying the representation quality threshold indicative of sufficient quality for disease detection;

in response to a determination that the quality score does not satisfy the quality threshold, discard the at least one representation; and in response to a determination that the quality score satisfies the quality threshold, provide an indication of the presence of the at least one disease.

11. The medical diagnostics system of claim 10, wherein the energy source comprises a light source, an x-ray source, or a magnetic source.

12. The medical diagnostics system of claim 10, wherein the energy source comprises a light source, the detector comprises an image detector array, the body part comprises an eye, and the at least one representation comprises at least one image of the eye.

13. The medical diagnostics system of claim 12, wherein the at least one image comprises a plurality of images determined from a video of the eye, and wherein discarding the at least one representation causes using of another image from the plurality of images for detecting the presence of the at least one disease.

14. The medical diagnostics system of claim 10, further comprising a display, wherein the electronic processing circuitry is further configured to provide the indication of the presence of the at least one disease on the display.

15. The medical diagnostics system of claim 10, wherein the electronic processing circuitry is configured to assess the quality of the at least one representation with another machine learning model different from the machine learning model.

16. The medical diagnostics system of claim 10, wherein discarding the at least one representation causes the at least one representation to be retaken.

17. The medical diagnostics system of claim 10, wherein the quality of the at least one representation is assessed based on at least one of a probability or a confidence score.

18. The medical diagnostics system of claim 10, wherein the certainty measure is based on at least one of a probability generated by the machine learning model or a confidence score generated by the machine learning model.

19. The medical diagnostics system of claim 10, wherein the electronic processing circuitry is configured to determine the quality score for the at least one representation by:

in response to the certainty measure for the presence of the at least one disease not satisfying a third certainty threshold indicative of insufficient likelihood that the at least one disease is present, setting the quality score to a value that does not satisfy the quality threshold irrespective of the quality of the at least one representation satisfying the quality threshold.

20. The medical diagnostics system of claim 10, wherein the electronic processing circuitry is configured to:

determine a confidence of the presence of the at least one disease based on a confidence score generated by the machine learning model and a confidence score generated by another machine learning model configured to assess the quality of the at least one representation; and output the confidence of the presence of the at least one disease along with the indication of the presence of the at least one disease.

* * * * *